United States Patent [19]

Boeve

[11] Patent Number: 4,548,716
[45] Date of Patent: Oct. 22, 1985

[54] METHOD OF PRODUCING ULTRAPURE, PYROGEN-FREE WATER

[76] Inventor: Lucas Boeve, 31 Winchester Oval, New Rochelle, N.Y. 10805

[21] Appl. No.: 634,304

[22] Filed: Jul. 25, 1984

[51] Int. Cl.[4] ............................. C02F 1/42; C02F 1/78
[52] U.S. Cl. .................................... 210/652; 210/668; 210/669; 210/760; 210/900
[58] Field of Search ............... 210/638, 652, 664, 668, 210/669, 685, 686, 748, 760, 192, 900

[56] References Cited

U.S. PATENT DOCUMENTS

| | | | |
|---|---|---|---|
| 799,605 | 9/1905 | Lester | 210/760 |
| 2,889,275 | 6/1959 | Moore | 210/760 |
| 3,276,458 | 10/1966 | Iversen et al. | 210/900 |
| 3,870,033 | 3/1975 | Faylor et al. | 210/900 |
| 4,069,153 | 1/1978 | Gunther | 210/760 |
| 4,160,727 | 7/1979 | Harris | 210/900 |
| 4,172,786 | 10/1979 | Humphrey et al. | 422/9 |
| 4,230,571 | 10/1980 | Dadd | 210/760 |
| 4,256,574 | 3/1981 | Bhargava | 210/760 |
| 4,273,660 | 6/1981 | Beitzel | 210/192 |
| 4,280,912 | 7/1981 | Berry et al. | 210/900 |

Primary Examiner—Ivars Cintins
Attorney, Agent, or Firm—Finnegan, Henderson Farabow, Garrett & Dunner

[57] ABSTRACT

A method of producing ultrapore, pyrogen-free water comprising providing a source of water; filtering the water to remove suspended solids and organics, deionizing the water to remove dissolved solids, and introducing substantially pure ozone into the deionized water at a concentration of at least two milligrams of ozone per liter of deionized water to thereby produce ultrapure, pyrogen-free water.

16 Claims, 1 Drawing Figure

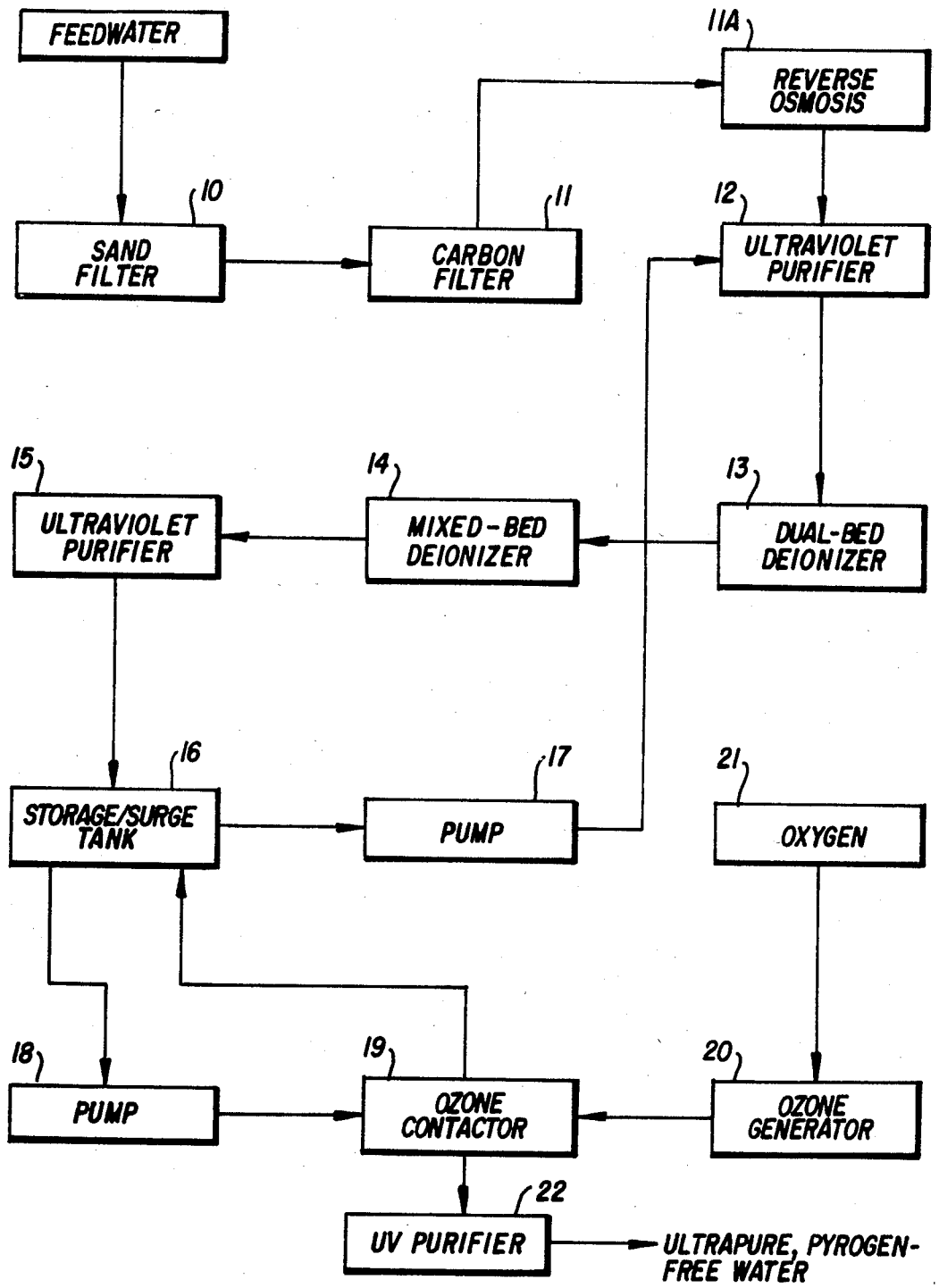

METHOD OF PRODUCING ULTRAPURE, PYROGEN-FREE WATER

BACKGROUND OF THE INVENTION

The present invention is directed to a method for purifying water and, more particularly, to a method for producing ultrapure, pyrogen-free water that can be used as a pharmaceutical solvent for injection into humans or other animals.

Since water is an excellent solvent, it finds many uses in the pharmaceutical and electronics industries, such as for rinsing, sterilizing and intravenous solutions. However, such uses for water require that the water be ultrapure, pyrogen-free. As used herein, "ultrapure, pyrogen-free" water is water that has a specific electrical resistance of at least 18 million ohms/cm (18 meg ohms/cm), and contains no pyrogens. Traditionally, water of such purity has been produced by distillation, which removes pyrogens, preceded by mixed-bed deionization. Indeed, the U.S. Food and Drug Administration ("FDA") requires that water for injection be water purified by either distillation or reverse osmosis. As used herein, "water for injection" is defined as water that satisfies the FDA's purity requirements for water for injection. Distillation, however, is a very energy consuming and costly method for producing water for injection.

U.S. Pat. No. 4,280,912 to Berry et al discloses producing water for injection by passing the water through the following treatment units: a bed of absorbent carbonaceous resin; an ion-exchange resin deionization bed; an ultra-violet energy source; and a resin polishing bed. However, Berry et al's feed water must have a minimum electrical resistance of 500,000 ohms/cm, which necessarily implies that Berry et al requires previously treated feed water. Single glass distillation, for example, produces water that has a specific electrical resistance of 500,000 ohms/cm.

It has been known for many years that ozone can be used in processes for treating water. For example, in U.S. Pat. No. 799,605 to Lester, an apparatus is disclosed to purify water that sequentially passes the water through an electrolytic chamber, an ozonizing chamber, a charcoal filter, a coarse sand filter, and a fine sand filter. However, Lester's system does not remove minerals and pyrogens and cannot produce ultrapure water.

U.S. Pat. No. 4,069,153 to Gunther discloses a method for purifying water that uses both ultraviolet radiation and ozone. More specifically, Gunther irradiates water with ultraviolet radiation of 1849 angstroms to convert oxygen dissolved in the water into ozone. According to Gunther, ozone enhances pyrogen destruction and provides a synergistic, or at least additive effect, with the ultraviolet radiation per se on the molecular alteration of pyrogens. However, Gunther's feed water is pretreated by distillation, and his method is not capable of producing ultrapure water.

Finally, U.S. Pat. No. 4,230,571 to Dadd discloses a method wherein ultraviolet radiation of 1850 angstroms generates ozone from air, the ozone generated is mixed with the water to be purified, and the water/ozone mixture is then subjected to ultraviolet radiation of 2600 angstroms. According to Dadd, the ultraviolet radiation has a catalytic effect on the reaction of ozone with bacteria, viruses and undesirable compounds in the water. Dadd's method does not produce pyrogen-free or ultrapure water.

SUMMARY OF THE INVENTION

The prior art discussed above that use ozone involve ozonators that produce ozone by irradiating air or oxygenerated water with an ultraviolet lamp. These methods produce a concentration of ozone of less than 0.2 milligrams per liter of water to be treated. Moreover, these prior art methods produce unwanted by-products from nitrogen when ozone is generated from air. Indeed, when ordinary tap water was used as a water source, I found that such a low ozone concentration in the presence of nitrogen from air actually created pyrogenic material. Quite surprisingly, however, I found that ultrapure, pyrogen-free water can be produced without the need for any pre-treatment, such as by distillation, reverse osmosis, or deionization, if the water is treated with substantially pure ozone at a concentration of at least 2 milligrams per liter of water.

More specifically, the present invention is directed to a method of producing ultrapure, pyrogen-free water, which is suitable for injection, comprising providing a source of water; filtering the water to remove suspended solids and organics; deionizing the water to remove dissolved solids; and introducing substantially pure ozone into the deionized water at a concentration of at least 2 milligrams of ozone per liter of deionized water to thereby produce ultrapure, pyrogen-free water. A particularly advantageous aspect of the present invention is that the source of water need not be pretreated, such as by distillation, reverse osmosis or deionization. Indeed, the source of water can be tap water, or even wastewater or seawater. If seawater is used, the seawater is preferably treated by reverse osmosis prior to deionizing the water.

In a preferred embodiment of the invention, the water is treated in an ultraviolet purifier prior to deionizing the water, and the ozone treated water is recirculated first to a storage/surge tank, and then to the ultraviolet purifier. In other preferred embodiments, the ozone is generated by subjecting substantially pure oxygen to a corona discharge, and the ozone treated water is treated in a final ultraviolet purifier to remove residual ozone.

As previously mentioned, present commercial methods for producing ultrapure, pyrogen-free water for injection require distillation. By use of the present invention, ultrapure, pyrogen-free water for injection can be produced at no more than 20% of the cost of the prior art distillation method. Although the present invention preferably can be used to produce water for injection, it also can be used for water reclamation and to clean up toxic liquid wastes.

BRIEF DESCRIPTION OF THE DRAWING

The sole drawing is a diagrammatic flow sheet of a preferred embodiment of the invention for producing ultra-pure, pyrogen-free water for injection.

DETAILED DESCRIPTION OF THE INVENTION

The invention will now be described in connection with a preferred embodiment of the invention diagrammatically depicted in the sole drawing.

A unique aspect of the present invention is that the source of water or feed water need not be pretreated, such as by distillation, reverse osmosis, or deionization.

Indeed, tap water, or even wastewater or seawater can be used as a source of water.

The feed water is first treated in a sand filter (10) and a carbon filter (11) to remove suspended solids and organics. The filters (10) and (11) are of conventional design and are commercially available. If seawater is used as feed water, the feed water is preferably next treated by conventional reverse osmosis (11A) to remove at least 90% of the minerals.

In order to remove bacteria, the feed water is passed to a conventional ultraviolet purifier (12). Preferably, ultra-violet energy is generated at a wavelength of 1850 angstroms.

The feed water is next passed to two conventional deionizers, a dual-bed deionizer (13) followed by a mixed-bed deionizer (14). The dual-bed deionizer removes dissolved solids to produce water having a specific resistance of up to one meg ohm/cm, whereas the mixed-bed deionizer removes dissolved solids to produce water having a specific resistance of up to 18 meg ohms/cm. After treatment by the mixed-bed deionizer, the water is ultrapure. The feed water is then passed to another conventional ultraviolet purifier (15) to maintain bacterial control prior to passing the feed water to a conventional storage/surge tank (16). A conventional pump (18) then distributes the feed water from tank (16) to a conventional ozone contactor (19).

A critical aspect of the present invention is the treatment of the feed water in ozone contactor (19). In order to obtain ultrapure, pyrogen-free water by the present invention, substantially pure ozone must be supplied to the ozone contactor. By "substantially pure ozone" is meant ozone which contains only trace amounts of impurities other than oxygen. Preferably, substantially pure ozone is produced by feeding oxygen, which is "pure" as defined by the U.S. Pharmacopoeia, from a pressure tank or pure oxygen generator (21) to an ozone generator (20). Preferably, the ozone generator is a corona arc.

Also critical to the present invention is that the concentration of ozone in the ozone contactor (19) be at least 2 milligrams of ozone per liter of deionized water. A corona arc is capable of producing such an ozone concentration, and is therefore preferred. By generating the aforementioned concentration of ozone in the ozone contactor (19), the ozone destroys the pyrogens, thereby producing ultrapure, pyrogen-free water.

The treatment of the feed water with ozone results in the generation of oxidation products. For example, if wastewater is used that contains synthetic organic compounds or associated pyrogens that contain heterocyclic compounds having ozone reactive functional groups, treatment with ozone at at least 2 milligrams/liter of water results in complete oxidation of these trace organics. In a preferred embodiment of the invention, a product recirculation loop is provided to remove such oxidation products. More specifically, ozone treated water is recycled from the ozone contactor (19) to the storage/surge tank (16) to maintain an ozone residual in the tank. A conventional process recirculation pump (17) then passes the water from tank (16) to the ultraviolet purifier (12). It is necessary to first pass the water through the ultraviolet purifier (12) to remove ozone since the high ozone concentration in the water would damage the resin in the deionizers. The oxidation products are then removed by deionizers (13) and (14).

Another advantage of the product recirculation loop is that heating is not required in the storage/surge tank (16) to maintain product purity since the residual ozone in tank (16) performs this function. Moreover, since heat is not required, the components of tank (16) and the product recirculation loop can be made of plastic instead of conventional stainless steel. Further, the product recirculation loop itself can be increased in size without fear of contamination because of the purifying presence of ozone.

If the ultrapure, pyrogen-free water that exits from the ozone contactor (19) is to be used for injection into humans or animals, it will be necessary to remove any residual ozone. Another important aspect of the present invention is the use of an ultraviolet purifier (22) to remove residual ozone from the purified water exiting from ozone contactor (19). Because of the high ozone concentration in the ozone contactor (19), there is insufficient oxygen in the purified water passing into the ultraviolet purifier (22) to produce ozone at the low ultraviolet energy that is used. Since ozone is unstable, with the ultraviolet purifier (22) producing ultraviolet energy at a wavelength of 1850 angstroms, the ultraviolet energy actually speeds up the conversion of ozone back to oxygen.

As those skilled in the art will appreciate, all equipment that comes into contact with the ozone, the ozone-containing water, or the ultrapure water, should be constructed of resistant materials, such as stainless steel, PVC or viton.

Water produced by the present invention has been examined by the Limulus Amebocyte Lysate (LAL) and rabbit tests, as well as by all of the other tests required for U.S. Pharmacopoeia water for injection, as specified by the FDA, and has been found to be ultrapure, pyrogen-free, and otherwise suitable for injection.

Although the above discussion has been specifically directed to producing ultrapure, pyrogen-free water for injection, one skilled in the art will appreciate that the present invention could also be used for water reclamation and to clean up toxic liquid wastes.

It will be apparent to those skilled in the art that various modifications and variations could be made in the process of the invention without departing from the scope or spirit of the invention.

What is claimed is:

1. A method of producing ultrapure, pyrogen-free water comprising:
   (a) providing a source of water;
   (b) filtering said water to remove suspended solids and organics;
   (c) deionizing said water to remove dissolved solids; and
   (d) introducing substantially pure ozone into said deionized water at a concentration of at least 2 milligrams of ozone per liter of deionized water to thereby produce ultrapure, pyrogen-free water.

2. The method of claim 1 wherein said deionizing of step (c) is performed by a dual-bed deionizer followed by a mixed-bed deionizer.

3. The method of claim 1 further comprising treating said water with ultraviolet radiation prior to step (c).

4. The method of claim 1 further comprising treating said water with ultraviolet radiation both prior to and after step (c).

5. The method of claim 1 further comprising treating said water with ultraviolet radiation after step (d) to remove residual ozone.

6. The method of claim 1 wherein said substantially pure ozone of step (d) is generated by subjecting substantially pure oxygen to a corona discharge.

7. The method of claim 1 wherein said source of water has not been pre-treated by distillation, reverse osmosis, or deionization.

8. The method of claim 1 wherein said source of water is tap water.

9. The method of claim 1 wherein said source of water is wastewater.

10. The method of claim 1 wherein said source of water is seawater.

11. The method of claim 10 further comprising treating said seawater by reverse osmosis prior to step (c).

12. A method of producing ultrapure, pyrogen-free water suitable for injection comprising:
    (a) providing a source of water;
    (b) filtering said water to remove suspended solids and organics;
    (c) deionizing said water to remove dissolved solids; and
    (d) introducing substantially pure ozone into said deionized water at a concentration of at least 2 milligrams of ozone per liter of deionized water to thereby produce ultrapure, pyrogen-free water suitable for injection.

13. A method of producing ultrapure, pyrogen-free water comprising:
    (a) providing a source of water;
    (b) filtering said water to remove suspensed solids and organics;
    (c) treating said water in an ultraviolet purifer;
    (d) deionizing said water to remove dissolved solids;
    (e) passing said deionized water into a storage/surge tank;
    (f) treating said deionized water in an ozone contactor by introducing substantially pure ozone into said deionized water at a concentration of at least 2 milligrams of ozone per liter of deionized water;
    (g) recirculating said ozone treated water first to said storage/surge tank and then to said ultraviolet purifier; and
    (h) removing ultrapure, pyrogen-free water from said ozone contactor.

14. The method of claim 13 further comprising treating said water in an ultraviolet purifier after step (d) but before step (e).

15. The method of claim 13 further comprising treating said water in an ultraviolet purifier after step (h) to remove residual ozone from the water.

16. A method of purifying water comprising:
    (a) providing a source of contaminated water;
    (b) filtering said water to remove suspended solids and organics;
    (c) deionizing said water to remove dissolved solids; and
    (d) introducing substantially pure ozone into said deionized water at a concentration of at least 2 milligrams of ozone per liter of deionized water.

* * * * *

UNITED STATES PATENT AND TRADEMARK OFFICE
CERTIFICATE OF CORRECTION

PATENT NO. : 4,548,716

DATED : October 22, 1985

INVENTOR(S) : Lucas Boeve

It is certified that error appears in the above-identified patent and that said Letters Patent is hereby corrected as shown below:

Column 5, line 31, delete "pl".

Signed and Sealed this

Fourth Day of February 1986

[SEAL]

Attest:

DONALD J. QUIGG

Attesting Officer

Commissioner of Patents and Trademarks